United States Patent [19]

Van Duren

[11] Patent Number: 5,303,712
[45] Date of Patent: Apr. 19, 1994

[54] CALIBRATION METHOD FOR SINGLE-BREATH CARBON MONOXIDE LUNG DIFFUSING CAPACITY TEST SYSTEM

[75] Inventor: Albert P. Van Duren, North St. Paul, Minn.

[73] Assignee: Medical Graphics Corporation, St. Paul, Minn.

[21] Appl. No.: 8,423

[22] Filed: Jan. 25, 1993

[51] Int. Cl.$^5$ .............................................. A61B 5/083
[52] U.S. Cl. .................................... 128/716; 128/719; 73/1 G
[58] Field of Search ........ 128/716, 719, 724, 725–730, 128/914, 205.17, 200.11–200.13, DIG. 12, 13; 137/861, 637, 637.05; 73/1 G, 23.2, 23.3

[56] References Cited

U.S. PATENT DOCUMENTS 5,119,825  6/1992  Huhn .
5,193,551  3/1993  Pilipski ............................ 128/719 X

OTHER PUBLICATIONS

"Single Breath Carbon Monoxide Diffusing Capacity (Transfer Factor)", American Review of Respiratory Diseases, 1987, vol. 136, pp. 1299–1307.

Primary Examiner—Angela D. Sykes
Attorney, Agent, or Firm—Haugen and Nikolai

[57] ABSTRACT

A method for testing/calibrating a system for performing single-breath carbon monoxide lung diffusing capacity measurements. By simulating a patient's lungs using a precision syringe for drawing a preanalysis gas mixture through the equipment (inspiration) and a modified scuba regulator valve or a solenoid valve with a purge button to simulate the expiration of a postanalysis gas through the system into a sampling chamber, the $DL_{co}$ measuring system performance can be assessed as a whole rather than as a collection of individual components.

2 Claims, 1 Drawing Sheet

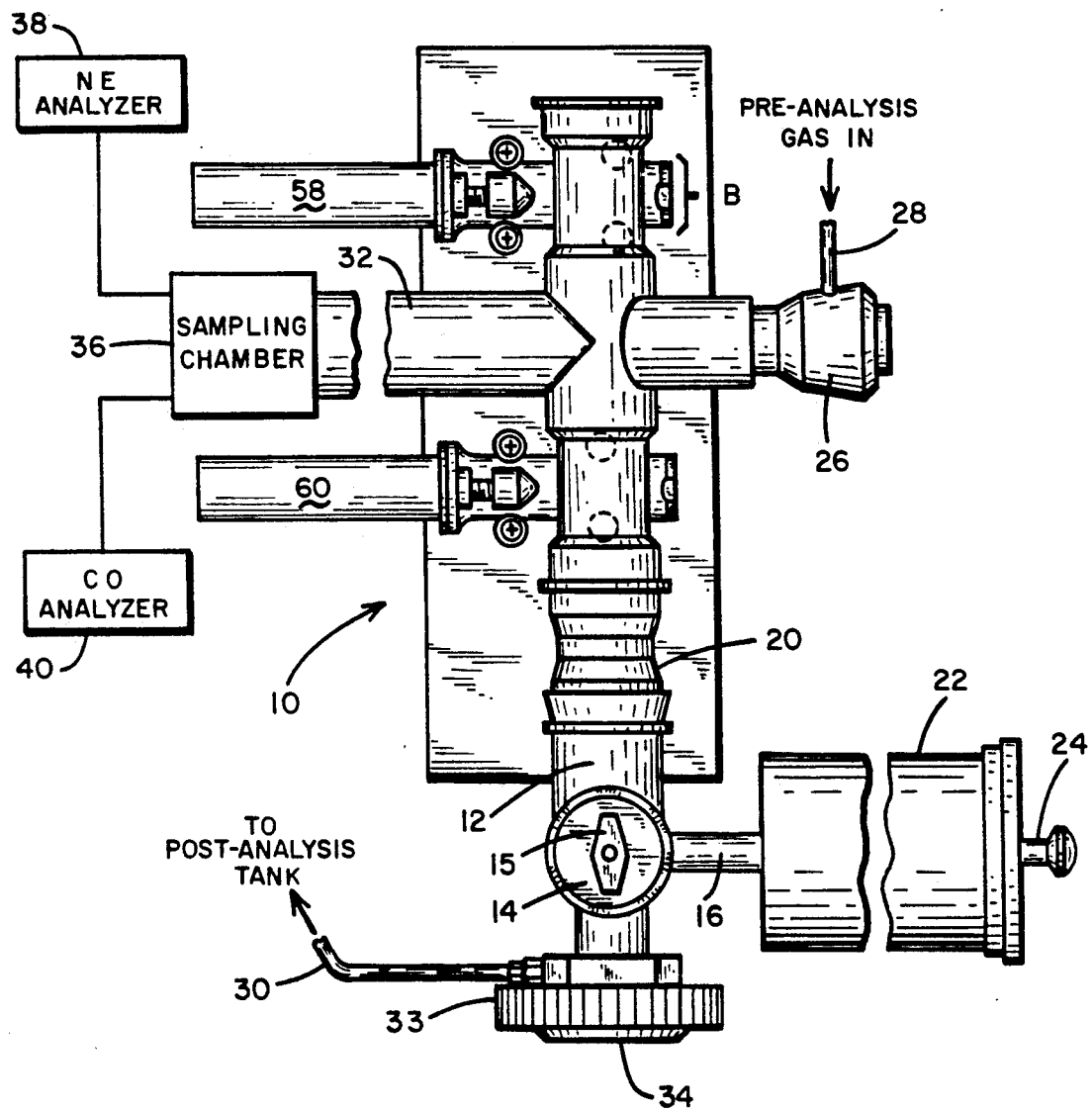

CALIBRATION METHOD FOR SINGLE-BREATH CARBON MONOXIDE LUNG DIFFUSING CAPACITY TEST SYSTEM

BACKGROUND OF THE INVENTION

I. Field of the Invention

This invention relates generally to pulmonary performance test equipment, and more particularly to a method and apparatus for calibrating such test equipment when used for measuring single-breath, carbon monoxide lung diffusion, commonly referred to by the symbol DL whereby the accuracy of the test is assured.

II. Discussion of the Prior Art

As is pointed out in an article entitled "Single Breath Carbon Monoxide Diffusing Capacity (Transfer Factor)", published in the 1987 edition of the *American Review of Respiratory Diseases*, Vol. 136, pp. 1299–1307, considerable difficulty has been experienced in obtaining accurate measurements of the diffusing capacity of a patient's lungs due to variabilities introduced by (1) test technique; (2) errors in gas analysis; and (3) the computation algorithms. A study discussed in the above-referenced article reveals the $DL_{co}$ measurements can vary between 53% and 125% due to errors in gas analysis. One cannot expect accurate measurements to be made if the equipment used in making those measurements is not properly calibrated.

In the Huhn U.S. Pat. No. 5,119,825, which is assigned applicant's assignee, there is described an apparatus useful in making $DL_{co}$ measurements. That patent describes a multifunction patient valve and how that valve can be sequenced to allow a preanalysis gas mixture including carbon monoxide, a tracer gas, such as neon or helium and air to be introduced through a mouthpiece into the patient's lungs, held there for a precise time interval, and then exhaled into a patient circuit leading to a sampling chamber. The as in the sampling chamber is then analyzed to determine the amount of the CO that had diffused through the lung tissue into the bloodstream during that precise interval by measuring the concentration of CO and the tracer gas exhaled into the sampling chamber.

The accurate determination of $DL_{co}$ requires the integration of data from several analyzers and transducers, as well as the coordination of the plumbing and valving which directs the gas flow to and from the patient. For this reason, verification of the performance of the individual components used to determine $DL_{co}$ does not establish the accuracy of the entire system. In accordance with the present invention, the accuracy of a test system is confirmed by presenting a precise volume of gas concentrations to the entire system in such a way as to simulate the entire $DL_{co}$ maneuver as it is performed by a patient. In this fashion, the system, as a whole, is tested and calibrated whereas in the past, only the individual components comprising the system had been individually tested in an attempt to provide assurance of system calibration.

SUMMARY OF THE INVENTION

It is accordingly a principal object of the present invention to provide a new and improved method for assessing the accuracy of a pulmonary performance test apparatus.

Another object of the invention is to provide a method for calibrating the equipment used to measure single-breath carbon monoxide lung diffusing capacity when operating as a complete system.

A typical system used to measure single-breath carbon monoxide diffusing capacity of a patient's lungs includes a multiport patient valve having a patient mouthpiece incorporating a flow meter coupled to a first port, a source of preanalysis gas coupled to a second port and a patient circuit including a sampling chamber coupled to a third port and with gas analyzing means coupled to the sampling chamber for measuring the concentration of CO and a tracer gas exhaled by the patient into the sampling chamber.

The method for calibrating that system in accordance with the present invention includes the steps of first drawing into a syringe a known volume of the preanalysis gas mixture of a tracer gas, carbon monoxide and air from a gas supply through a first portion of the patient valve which includes the mouthpiece. That known volume is then retained in the syringe for a predetermined time interval corresponding to the time that a patient would normally hold the gas mixture in his/her lungs. At the end of this time interval, a bolus of a postanalysis gas mixture of the tracer gas, carbon monoxide and air is introduced through the mouthpiece and the patient circuit into the sampling chamber. The postanalysis gas mixture is selected to contain amounts of CO and a tracer gas in air which would produce clinically reasonable $DL_{co}$ values at typical inspired volumes and breath-hold times. The gas analyzing means is then allowed to measure the constituents of the postanalysis gas mixture contained within the sampling chamber to obtain $DL_{co}$ and alveolar volume readings. These readings are subsequently compared with target $DL_{co}$ and alveolar volume values computed using known formulas which take into account ambient barometric pressure, temperature, the known volume of preanalysis gas mixture and the time interval to determine any differences between the measured readings and the computed target values.

BRIEF DESCRIPTION OF THE DRAWING

The foregoing features, objects and advantages of the invention will become apparent to those skilled in the art from the following detailed description of a preferred embodiment, especially when considered in conjunction with the accompanying drawing which shows a top plan view of a typical $DL_{co}$ performance measuring system and the additional devices used in carrying out the calibration method in accordance with the present invention.

DESCRIPTION OF THE PREFERRED EMBODIMENT

Referring to the drawing, there is indicated generally by numeral 10 a multifunction patient valve which is substantially identical to that described in the aforereferenced Huhn U.S. Pat. No. 5,119,825, the teachings of which are hereby incorporated by reference as if set out in full herein. In that the Huhn patent fully describes the manner in which the multifunction patient valve 10 can be used in performing the single-breath carbon monoxide lung diffusing capacity test, it need not be repeated here.

In calibrating the system, the common port 12 of a three-way stopcock valve 14 is securely attached to the mouth piece member 20 of the multifunction patient valve assembly 10. It is important that the attachment be such that no leakage can occur between the common port 12 of the three-way stopcock 14 and the annular opening of the mouthpiece member 20. Coupled to a first port of the stopcock 14 by a tube 16 is a large volume syringe 22 having volume markings (not shown) embossed on the plunger shaft 24. A supply tank containing a preanalysis gas mixture is connected by a hose 28 to the demand valve 26. Likewise, a supply tank (not shown) containing a postanalysis gas mixture is connected by a hose 30 to a modified scuba regulator 33 which may typically be a Dacor XLP Pacer ™ regulator which includes a purge button 34. This Dacor regulator is modified by removing its exhaust manifold and by plugging its exhaust port with a plastic window and then exchanging a rubber O-ring on its effort control shaft to make the entire valve assembly 33 airtight. The modified scuba (Dacor regulator) valve may be replaced by an electronically operated solenoid valve.

The preanalysis gas mixture contains concentrations of the tracer gas (typically helium or neon) and CO which are normally used when the system under test is being used with a patient. The postanalysis mixture fed into the tube 30 is selected to contain amounts of CO and tracer gas which will produce clinically reasonable $DL_{co}$ values at typical inspired volumes and breath-hold times. For example, but with no limitation intended, the postanalysis mixture may contain one-half as much CO and 3/5ths as much tracer gas as does the preanalysis mixture coupled to the hose 28.

In performing the calibration with the equipment shown in FIG. 1, the valve handle 15 on the three-way stopcock 14 is positioned so that the syringe 22 and the common port 12 communicate with one another. With the clamps 58 and 60 unactivated, the plunger 24 on the syringe 22 may be pushed back and forth reciprocally to simulate tidal breathing. Next, the clamp 58 is actuated to pinch off the patient valve in zone B. Now, as the plunger 24 is pulled out, a volume of preanalysis gas will be drawn through the demand valve 26, the mouthpiece 20 and the three-way stopcock 14 into the syringe 22. The markings (not shown) on the plunger shaft 24 can be used to indicate precisely the volume of gas drawn into the syringe.

Following this inspiration of the preanalysis gas, the three-way stopcock is rotated so that the scuba valve 33 and the common port 12 are connected. At the end of an appropriate breath-hold time, e.g., 10 seconds, the purge button 34 on the scuba regulator valve 33 is depressed, allowing a bolus of postanalysis gas to flow through the hose 30, the valve 33, the stopcock 14, the mouthpiece 20, the patient valve 10 into the patient circuit 33 leading to a sampling chamber 36.

Once the postanalysis gas is in the sampling chamber, the neon analyzer 38 and the carbon monoxide analyzer 40 forming a part of the pulmonary performance test unit are allowed to perform a normal analysis of the expired gas.

The basic formula for calculating $DL_{co}$ is as follows:

$$DL_{co} = V_{A\,STPD} \times \frac{60}{t} \times \frac{1}{P_B - 47} \ln \frac{F_{ACO_o}}{F_{ACO_t}}$$

$$\text{where } V_{A\,STPD} = V_{I\,STPD} \times \frac{F_{IHe}}{F_{AHe}}$$

$$\text{and where } F_{ACO_o} = F_{ICO} \times \frac{F_{AHe}}{F_{IHe}}$$

$V_{A\,STPD}$ is alveolar volume at standard conditions
$t$ = breath-hold time in seconds.
$P_B$ = barometric pressure
$F_{ACO}$ = fraction of CO in alveolar gas
$V_{I\,STPD}$ = inspired volume at standard conditions
$F_{IHE}$ = fraction of inspired helium tracer
$F_{AHE}$ = fraction of helium in alveolar gas
$F_{ICO}$ = fraction of CO inspired.

A computation is then made of the target $DL_{co}$ and $V_A$ using the ambient barometric pressure, temperature, $V_I$, and breath-hold time. The computed target values are then compared to the values returned by the instrument under test. The approximate theoretical accuracy of the test method of the present invention is no worse than ±0.5% of the target $DL_{co}$ when a 3.000 liter syringe determines $V_I$ and ±0.2% with a 7.000 liter inspired gas volume.

It can be seen from the foregoing description that the method and apparatus of the present invention allows precise calibration of the $DL_{co}$ equipment by effectively simulating its normal operation with the syringe 22 functioning as a patient's lungs when inhaling and the scuba valve 33 acting as the lungs during exhalation. In this fashion, the test or calibration of the system is performed on the entire system with all of its parts interconnected, rather than as with the prior art where various individual parts were tested.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A method for calibrating a system used to measure single-breath carbon monoxide diffusing capacity of a patient's lungs ($DL_{co}$), said system being of the type including a multiport patient valve having a patient mouthpiece coupled to a first port, a source of a preanalysis gas mixture of a tracer gas, carbon monoxide and air in a known concentration of each constituent coupled to a second port and a patient circuit including a sampling chamber coupled to a third port and gas analyzing means coupled to said sampling chamber, comprising the steps of:
 (a) drawing a known volume of said preanalysis gas mixture from a source through a first portion of said system into a syringe;
 (b) retaining said known volume in said syringe for a predetermined time interval;
 (c) introducing a bolus quantity of a postanalysis gas mixture of said tracer gas, carbon monoxide and air of a known concentration of constituents, said concentration being independent of any dilutional change and extent of mixing, through said patient circuit into said sampling chamber;
 (d) allowing said gas analyzing means to measure said constituents of said postanalysis gas mixture contained within said sampling chamber to obtain $DL_{co}$ and alveolar volume ($V_A$) readings; and
 (e) comparing the results of steps of (d) with target $DL_{co}$ and $V_A$ values computed by using ambient barometric pressure, temperature, said known volume and concentration of preanalysis and postanalysis gas mixtures and said time interval to determine any differences between said readings and said target values.

2. The method as in claim 1 wherein said postanalysis gas mixture contains approximately one-half as much carbon monoxide and approximately three-fifths as much tracer gas as in said preanalysis gas mixture.

* * * * *